United States Patent [19]
Wild et al.

[11] Patent Number: 5,492,918
[45] Date of Patent: Feb. 20, 1996

[54] USE OF SUBSTITUTED CHROMANS, SOME OF WHICH ARE KNOWN, AS MEDICAMENTS, NEW ACTIVE COMPOUNDS AND PROCESSES FOR THEIR PREPARATION

[75] Inventors: Hanno Wild; Wolfgang Bender; Dieter Häbich, all of Wuppertal; Hans-Georg Heine, Krefeld; Siegfried Raddatz, Köln; Wolfgang Röben, Bergisch Gladbach; Jutta Hansen, Wuppertal; Arnold Paessens, Haan, all of Germany

[73] Assignee: Bayer Aktiengesellschaft, Leverkusen, Germany

[21] Appl. No.: 251,986

[22] Filed: Jun. 1, 1994

[30] Foreign Application Priority Data

Jun. 8, 1993 [DE] Germany ............ 43 19 038.3

[51] Int. Cl.$^6$ ............ A61K 31/445; C07D 405/14
[52] U.S. Cl. ............ 514/322; 514/320; 546/196; 546/199
[58] Field of Search ............ 546/196, 199; 514/320, 322

[56] References Cited

U.S. PATENT DOCUMENTS

| | | | |
|---|---|---|---|
| 4,957,928 | 9/1990 | Frostl | 514/318 |
| 4,977,166 | 12/1990 | Hardy | 514/323 |
| 4,997,836 | 3/1991 | Sugihara | 514/253 |
| 5,030,639 | 7/1991 | Davis | 514/322 |
| 5,240,943 | 8/1993 | Desai | 514/320 |
| 5,371,094 | 12/1994 | Heine | 514/323 |

FOREIGN PATENT DOCUMENTS 0546388   6/1993   European Pat. Off. .

OTHER PUBLICATIONS

Journal of Medicinal Chemistry, vol. 34, No. 8, Aug. 1991; Perspective, "HIV Protease: A Novel Chemotherapeutic Target for AIDS", J. R. Huff, pp. 2306–2314.

Bioorganic & Medicinal Chemistry Letters, vol. 2, No. 6, pp. 541–546, 1992; "The Use of HIV–1 Protease Structure in Inhibitor Design", R. E. Babine et al.

J. Med. Chem., 1992, vol. 35, pp. 2525–2533; "A Series of Potent HIV–1 Protease Inhibitors Containing a Hydroxyethyl Secondary . . . ", T. J. Tucker et al.

The EMBO Journal, vol. 7, No. 6, pp. 1785–1791, 1988; "Partial purification and substrate analysis of bacterially–express HIV . . . ", J. Hansen et al.

Journal of Virological Methods, vol. 22, 1988, pates 309–317; "Antibodies to Human Cytomegalovirus Structural Polypeptides . . . ", M. P. Landini et al.

*Primary Examiner*—Ceila Chang
*Attorney, Agent, or Firm*—Sprung Horn Kramer & Woods

[57] ABSTRACT

The present invention relates to the use of substituted chromans of the general formula (I)

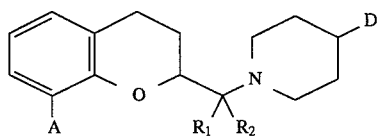

in which
the substituents have the meaning indicated in the description, for the production of medicaments, in particular as HIV protease-inhibiting agents, new active compounds and processes for their preparation.

2 Claims, No Drawings

USE OF SUBSTITUTED CHROMANS, SOME OF WHICH ARE KNOWN, AS MEDICAMENTS, NEW ACTIVE COMPOUNDS AND PROCESSES FOR THEIR PREPARATION

The invention relates to the use of substituted chromans, some of which are known, as medicaments, in particular as HIV protease-inhibiting agents, new active compounds and processes for their preparation.

It has been found that the substituted chromans of the general formula (I)

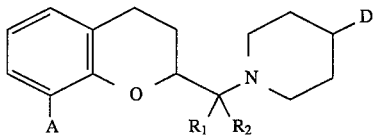

in which

A represents hydrogen, hydroxyl or straight-chain or branched alkoxy having up to 8 carbon atoms, $R^1$ and $R^2$ represent hydrogen, or $R^1$ and $R^2$ together represent, the —C=O group, D represents a radical of the formula —$NR^3$—CO—$NR^4R^5$ or

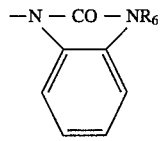

in which $R^3$, $R^4$ and $R^6$ are identical or different and denote hydrogen or straight-chain or branched alkyl having up to 6 carbon atoms, $R^5$ denotes aryl having 6 to 10 carbon atoms, which is optionally substituted up to 3 times by identical or different substituents from the series consisting of halogen, hydroxyl, carboxyl, trifluoromethyl and trifluoromethoxy, by straight-chain or branched acyl, alkoxy or alkoxycarbonyl in each case having up to 8 carbon atoms or by straight-chain or branched alkyl or alkenyl in each case having up to 8 carbon atoms, which for their part can be substituted by hydroxyl or carboxyl or by straight-chain or branched alkoxy or alkoxycarbonyl in each case having up to 6 carbon atoms, and their racemates, enantiomers and salts, surprisingly have a strong inhibiting action against HIV protease and are thus suitable for use in the control of HIV.

Preferably used compounds are those of the general formula (I) in which

A represents hydrogen, hydroxyl or straight-chain or branched alkoxy having up to 6 carbon atoms, $R^1$ and $R^2$ represent hydrogen, or $R^1$ and $R^2$ together represent the —C=O group, D represents a radical of the formula —$NR^3$—CO—$NR^4R^5$ or

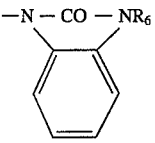

in which $R^3$, $R^4$ and $R^6$ are identical or different and denote hydrogen or straight-chain or branched alkyl having up to 4 carbon atoms, $R^5$ denotes phenyl or naphthyl, each of which is optionally substituted up to 2 times by identical or different substituents from the series consisting of fluorine, chlorine, bromine, hydroxyl, carboxyl, trifluoromethyl and trifluoromethoxy, by straight-chain or branched acyl, alkoxy or alkoxycarbonyl in each case having up to 6 carbon atoms, or by straight-chain or branched alkyl or alkenyl in each case having up to 6 carbon atoms, which for their part can be substituted by hydroxyl or carboxyl or by straight-chain or branched alkoxy or alkoxycarbonyl in each case having up to 4 carbon atoms, and their racemates, enantiomers and salts, in the control of HIV.

Particularly preferably used compounds are those of the general formula (I) in which A represents hydrogen, hydroxyl or straight-chain or branched alkoxy having up to 5 carbon atoms, $R^1$ and $R^2$ represent hydrogen, or $R^1$ and $R^2$ together represent the —C=O group, D represents a radical of the formula —$NR^3$—CO—$NR^4R^5$ or

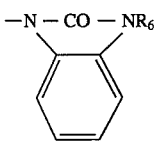

in which $R^3$, $R^4$ and $R^6$ are identical or different and denote hydrogen or straight-chain or branched alkyl having up to 3 carbon atoms, $R^5$ denotes phenyl or naphthyl, each of which is optionally substituted up to 2 times by identical or different substituents from the series consisting of fluorine, chlorine, bromine, trifluoromethyl and trifluoromethoxy, by straight-chain or branched acyl, alkoxy or alkoxycarbonyl in each case having up to 5 carbon atoms, or by straight-chain or branched alkyl or alkenyl in each case having up to 5 carbon atoms, which for their part can be substituted by hydroxyl or carboxyl or by straight-chain or branched alkoxy or alkoxycarbonyl in each case having up to 3 carbon atoms, and their racemates, enantiomers and salts, in the control of HIV.

The invention additionally relates to new compounds of the general formula (Ia)

(Ia) [structure]

in which

A' represents hydrogen, hydroxyl or straight-chain or branched alkoxy having up to 8 carbon atoms, $R^{1'}$ and $R^{2'}$ represent hydrogen, or $R^{1'}$ and $R^{2'}$ together represent the —C=O group, D represents a radical of the formula —$NR^{3'}$—CO—$NR^{4'}R^{5'}$ or $$-N-CO-NR^{6'}$$ [with fused benzene ring]

in which $R^{3'}$, $R^{4'}$ and $R^{6'}$ are identical or different and denote hydrogen or straight-chain or branched alkyl having up to 6 carbon atoms, $R^{5'}$ denotes aryl having 6 to 10 carbon atoms, which is optionally substituted up to 3 times by identical or different substituents from the series consisting of halogen, hydroxyl, carboxyl, trifluoromethyl and trifluoromethoxy, by straight-chain or branched acyl, alkoxy or alkoxycarbonyl in each case having up to 8 carbon atoms or by straight-chain or branched alkyl or alkenyl in each case having up to 8 carbon atoms, which for their part can be substituted by hydroxyl or carboxyl or by straight-chain or branched alkoxy or alkoxycarbonyl in each case having up to 6 carbon atoms, and their racemates, enantiomers and salts, with the proviso that D' must not represent the radical of the formula

[structure: benzimidazolone-like]

if, in the case of the racemate and of the enantiomers, A', $R^{1'}$ and $R^{2'}$ denote hydrogen, or in the case of the racemate, A' represents methoxy and $R^1$ and $R^2$ denote hydrogen.

Physiologically acceptable salts of the substituted chromans of the general formulae (I) and (Ia) can be salts of the substances according to the invention with mineral acids, carboxylic acids or sulphonic acids.

Particularly preferred salts are e.g. those with hydrochloric acid, hydrobromic acid, sulphuric acid, phosphoric acid, methanesulphonic acid, ethanesulphonic acid, toluenesulphonic acid, benzenesulphonic acid, naphthalenesulphonic acid, acetic acid, propionic acid, lactic acid, tartaric acid, citric acid, fumaric acid, maleic acid or benzoic acid.

Salts which can be mentioned are salts with customary bases, such as, for example, alkali metal salts (e.g. sodium or potassium salts), alkaline earth metal salts (e.g. calcium or magnesium salts) or ammonium salts derived from ammonia or organic amines such as, for example, diethylamine, triethylamine, ethyldiisopropylamine, procaine, dibenzylamine, N-methylmorpholine, dihydroabietylamine, 1-ephenamine or methyl-piperidine.

The compounds of the general formulae (I) and (Ia) according to the invention can exist in stereoisomeric forms which either behave as image and mirror image (enantiomers), or which do not behave as image and mirror image (diastereomers). The invention relates both to the antipodes and to the racemic forms and the diastereomeric mixtures. Like the diastereomers, the racemic forms can be separated into the stereoisomerically homogeneous constituents in a known manner.

Processes for the preparation of the compounds of the general formulae (I) and (Ia) according to the invention have additionally been found, characterized in that in the case in which D and D' in each case correspondingly represent the radicals of the formulae —$NR^3$—CO—$NR^4R^5$ or —$NR^{3'}$—CO—$NR^{4'}R^{5'}$

[A] compounds of the general formula (II)

$$E-N\underset{\phantom{xx}}{\bigcirc}-NHR_7 \quad (II)$$

in which $R^7$ includes the abovementioned meaning of $R^3$ and $R^{3'}$ and

E represents an amino protective group, preferably benzyl, are first converted by reaction with isocyanates of the general formula (III)

$$O=C=N-R^8 \quad (III)$$

in which $R^8$ includes the abovementioned meaning of $R^5$ and $R^{5'}$, in inert solvents, if appropriate in the presence of a base and/or of an auxiliary, into the compounds of the general formula (IV)

$$HN\underset{\phantom{xx}}{\bigcirc}-NR_7-CO-NHR_8 \quad (IV)$$

in which $R^7$ and $R^8$ have the abovementioned meaning, and these are then reacted with compounds of the general formula (V)

(V) [structure with chroman-CO₂H and L substituent]

in which

L includes the abovementioned meaning of A and A', but does not represent hydroxyl, likewise in inert solvents, if appropriate in the presence of a base and of an auxiliary, or

[B] in the case in which D and D' in each case correspondingly represent the radicals of the formulae

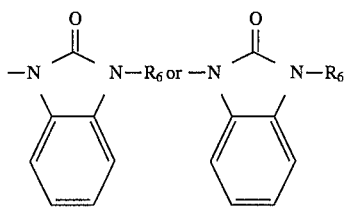

compounds of the general formula (V) are reacted with compounds of the general formula (VI)

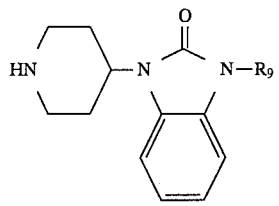
(VI)

in which $R^9$ includes the abovementioned meaning of $R^6$ and $R^{6'}$, in inert solvents, in the presence of a base and/or auxiliary, and if $R^1/R^{1'}$, $R^2$=H the carbonyl function is reduced according to customary methods, and if L=OH, the corresponding methoxy compound is cleaved with acids, and if L=alkoxy, the corresponding hydroxyl compounds are etherified, and if $R^7$, $R4/R^{4'}$ and/or $R^9 \neq H$, an alkylation is optionally carried out.

The processes according to the invention can be illustrated by way of example by the following reaction scheme:

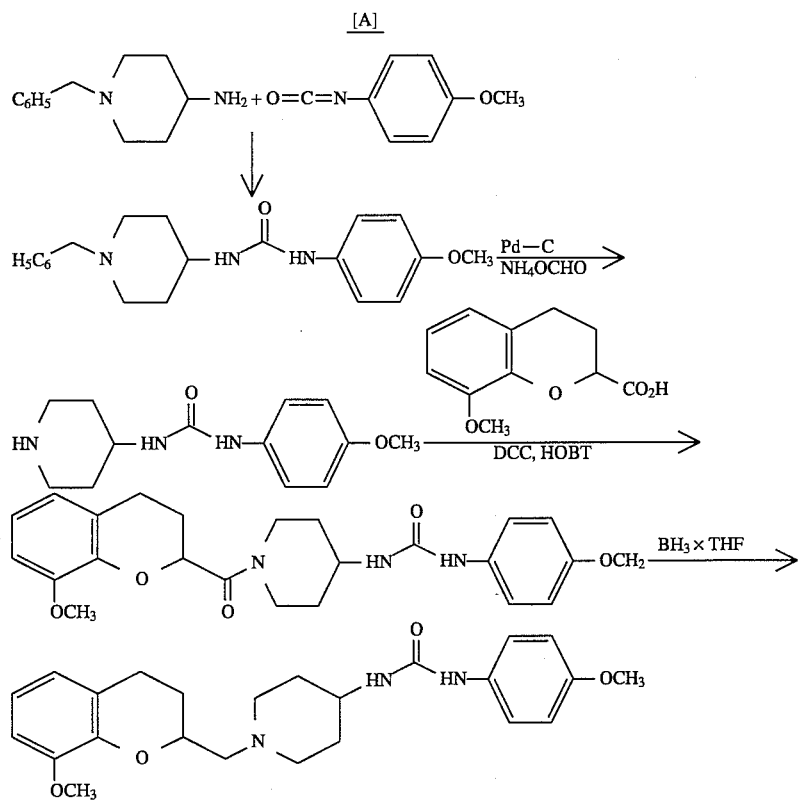

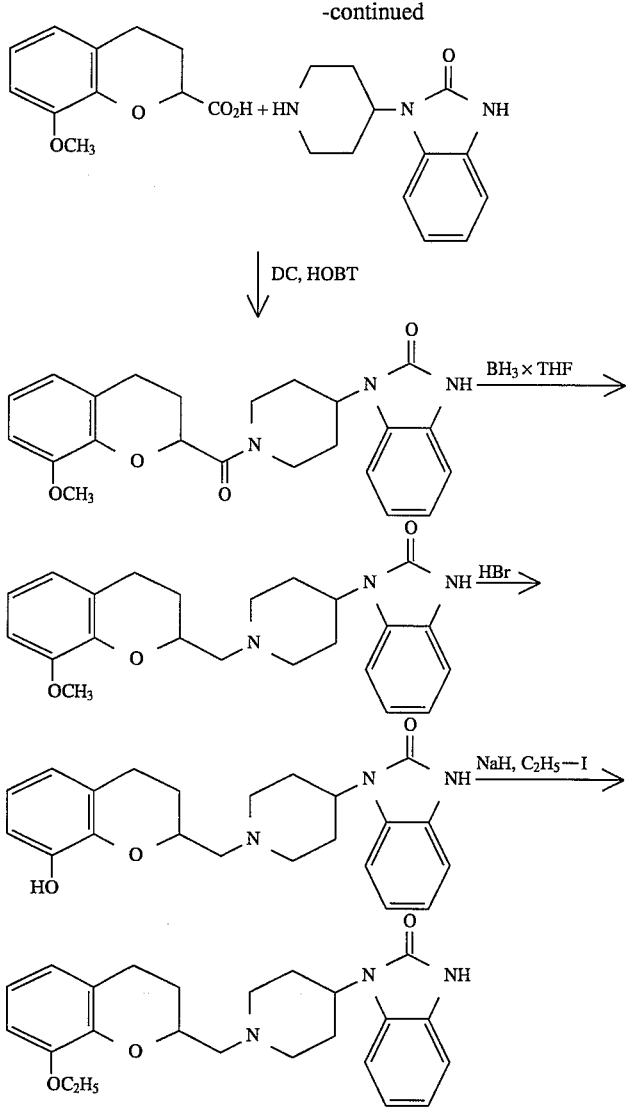

Amino protective groups in the context of the invention are the customary amino protective groups used in peptide chemistry. These preferably include: benzyloxycarbonyl, tert-butoxycarbonyl and allyloxycarbonyl.

Suitable solvents are the customary inert solvents which do not change under the reaction conditions. These preferably include organic solvents such as ethers e.g. diethyl ether, glycol monomethyl or dimethyl ether, dioxane or tetrahydrofuran, or hydrocarbons such as benzene, toluene, xylene, cyclohexane or mineral oil fractions or halogenohydrocarbons such as methylene chloride, chloroform, carbon tetrachloride, or dimethyl sulphoxide, dimethylformamide, hexamethylphosphoramide, ethyl acetate, pyridine, triethylamine or picoline. It is also possible to use mixtures of the solvents mentioned. Dichloromethane, chloroform, dimethylformamide or tetrahydrofuran is particularly preferred.

Bases employed for the processes according to the invention can in general be inorganic or organic bases. These preferably include alkali metal hydroxides such as, for example, lithium hydroxide, sodium hydroxide or potassium hydroxide, alkaline earth metal hydroxides such as, for example, barium hydroxide, alkali metal carbonates such as sodium carbonate or potassium carbonate, alkaline earth metal carbonates, such as calcium carbonate or caesium carbonate, or alkali metal or alkaline earth metal alkoxides or amides such as sodium methoxide or potassium methoxide, sodium ethoxide or potassium ethoxide or potassium tert-butoxide, or lithium diisopropylamide (LDA), or organic amines (trialkyl-($C_1$–$C_6$)amines) such as triethylamine, or heterocycles such as 1,4-diazabicyclo[2.2.2]octane (DABCO), 1,8-diazabicyclo[5.4.0]undec-7-ene (DBU), pyridine, diaminopyridine, N-methylpiperidine or morpholine. It is also possible to employ as bases alkali metals, such as sodium or their hydrides such as sodium hydride. Triethylamine or N-methylmorpholine is preferred.

In general, the base is employed in an amount from 0.05 mol to 10 mol, preferably from 1 mol to 2 mol, in each case relative to 1 mol of the compounds of the formulae (III), (V) and (VI).

The processes according to the invention are in general carried out in a temperature range from −100° C. to +100° C., preferably from 0° C. to 80° C.

The processes according to the invention are in general carried out at normal pressure. However, it is also possible to carry out the processes at elevated pressure or at reduced pressure (e.g. in a range from 0.5 to 5 bar).

Auxiliaries employed are preferably condensing agents which can also be bases, in particular if the carboxyl group is present activated as the anhydride. Those preferred here are the customary condensing agents such as carbodiimides e.g. N,N'-diethyl-, N,N'-diisopropyl- and N,N'-dicyclohexylcarbodiimide, N-(3-dimethylaminoisopropyl)-N'-ethyl-carbodiimide hydrochloride, N-cyclohexyl-N'-(2-morpholinoethyl)-carbodiimide metho-p-toluenesulphonate, or carbonyl compounds such as carbonyldiimidazole, or 1,2-oxazolium compounds such as 2-ethyl-5-phenyl-1,2-oxazolium-3-sulphate or 2-tert-butyl- 5-methyl-isoxazolium perchlorate, or acylamino compounds such as 2-ethoxy-1-ethoxycarbonyl-1,2-dihydroquinoline, or propanephosphonic anhydride, or isobutyl chloroformate, or benzotriazolyloxy-tris (dimethylamino) phosphonium hexafluorophosphate or 1-hydroxybenzotriazole.

Additionally, for example, alkali metal carbonates, e.g. sodium carbonate or hydrogen carbonate or potassium carbonate or hydrogen carbonate, or organic bases such as trialkylamines, e.g. triethylamine, ethyldiisopropylamine, N-ethylmorpholine, N-methylpiperidine or N-methylmorpholine can be employed. N-Methylmorpholine is preferred.

The auxiliaries are employed in an amount from 1.0 mol to 3.0 mol, preferably 1.0 to 1.2 mol, relative in each case to 1 mol of the compounds of the general formulae (III), (IV) and (VI).

The reactions are carried out in a temperature range from $-30°$ C. to 100° C., preferably at 0° C. to 30° C. and at normal pressure.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is also possible to employ mixtures of the solvents mentioned.

The hydrolysis is in general carried out in a temperature range from 0° C. to +100° C. preferably from +20° C. to +80° C.

In general, hydrolysis is carried out at normal pressure. However, it is also possible to work at reduced pressure or at elevated pressure (e.g. from 0.5 to 5 bar).

When carrying out hydrolysis, the base is in general employed in an amount from 1 to 3 mol, preferably from 1 to 1.5 tool, relative to 1 mol of the ester. Molar amounts of the reactants are particularly preferably used.

Hydrolysis of tert-butyl esters is in general carried out using acids, such as, for example, hydrochloric acid or trifluoroacetic acid, in the presence of one of the abovementioned solvents and/or water or mixtures thereof, preferably with dioxane, tetrahydrofuran or dichloromethane.

The removal of the amino protective groups can be carried out by a customary method using acids, such as, for example, hydrochloric acid or trifluoroacetic acid.

Removal of the amino protective groups is carried out in a known manner under acidic or basic conditions, or reductively by catalytic or transfer hydrogenation, for example using Pd/C in organic solvents such as ethers, e.g. tetrahydrofuran or dioxane, or alcohols e.g. methanol, ethanol or isopropanol.

Hydrogenation is in general carried out in a temperature range from 0° C. to 80° C. preferably from 0° C. to 40° C.

In general, hydrogenation is carried out at elevated pressure from 2 bar to 8 bar, preferably from 3 to 5 bar.

Removal of the benzyl protective groups is preferably carried out using ammonium formate/palladium/C in ethanol/water in a temperature range from 20° C. to 80° C., preferably at 50° C. and at normal pressure.

Alkylation of amino groups is carried out either using sulphonic acid esters or substituted or unsubstituted $(C_1–C_8)$-dialkyl or $(C_1–C_8)$-diaryl sulphonates, preferably methyl iodide or dimethyl sulphate, or using formaldehyde/sodium borohydride in one of the abovementioned ethers, preferably tetrahydrofuran, in the presence of acids.

Alkylation is in general carried out in one of the abovementioned solvents, preferably in dimethylformamide in a temperature range from 0° C. to +70° C., preferably from 0° C. to +30° C. and at normal pressure.

Reduction of the carbonyl functions is in general carried out using reducing agents, such as, for example, lithium aluminium hydride, using borane solution in tetrahydrofuran or using borane-dimethyl sulphide (complex in tetrahydrofuran) in a temperature range from 0° C. to 70° C., preferably from +20° C. to +65° C. and at normal pressure and subsequent taking up in acids. Borane solution in tetrahydrofuran is preferred.

Suitable acids for individual process steps are in general protic acids such as, for example, hydrochloric acid or sulphuric acid. Sulphuric acid is preferably employed.

The acid is in general employed in an amount from 1 mol to 20 mol, preferably from 1 mol to 5 mol, in each case relative to 1 mol of the reactant.

The etherification of the compounds according to the invention (A/A'(L)≠OH) is carried out using one of the abovementioned alkylating agents in the presence of one of the abovementioned solvents and bases, preferably using potassium tert-butoxide and sodium hydride.

The reactions are in general carried out in a temperature range from $-20°$ C. to +80° C., preferably from 0° C. to +60° C.

In general, the reaction is carried out at normal pressure. However, it is also possible to work at reduced pressure or at elevated pressure (e.g. from 0.5 to 5 bar). The liberation of the hydroxyl function (A/A'(L)=OH is carried out using hydrogen acids, preferably hydrobromic acid at boiling heat and normal pressure.

The compounds of the general formulae (IV) and (VI) are known in some cases or are new and can then be prepared, for example, as described above.

The compounds of the general formulae (II), (III) and (V) are known per se.

The inhibitors of the general formula (I) and the new compounds of the general formula (Ia) described here are inhibitors of HIV protease and can be employed as such for all purposes for which enzyme inhibitors are suitable. This is, for example, use in diagnostics to improve the precision and selectivity of enzyme activity measurements. In affinity chromatography, they can be used as an affinity label and in research they can be used for elucidating reaction mechanisms and the specificity of enzymatic reactions.

Moreover, it has surprisingly been found that the compounds of the general formulae (I) and (Ia) have an action against retroviruses. This is confirmed by an HIV-specific protease enzyme test.

The results of the examples shown below were determined by the HIV test system described in the following bibliographical references [cf. Hansen, J., Billich, S., Schulze, T., Sukrow, S. and Mölling, K. (1988), EMBO Journal, Vol, 7, No. 6, pp. 1785–1791]: purified HIV protease was incubated with synthetic peptide which imitated a cleavage site in the Gag precursor protein and is an in vivo cleavage site of HIV protease. The resultant cleavage products of the synthetic peptide were analysed by means of reverse phase high performance liquid chromatography (RP-HPLC). The $IC_{50}$ values indicated relate to the substance concentration which, under the abovementioned test conditions, causes a 50% inhibition of protease activity.

TABLE 1

| Ex. No. | % Inhibition at 200 µg/ml | IC$_{50}$ (µM) |
|---|---|---|
| 1 | 99 | |
| 21 | 65 | |
| 24 | 99 | |
| 25 | 74 | |
| 27 | 81 | |
| 28 | 94 | |
| 30 | 99 | 0.0002 |
| 33 | 99 | |

HIV infection in cell culture

The HIV test was carried out with slight modifications by the method of Pauwels et al,. [cf. Journal of Virological Methods 20, (1988), 309–321].

Normal human blood lymphocytes (PBLs) were concentrated on Ficoll Hypaque and stimulated with phytohaemagglutinin (90 µg/ml) and interleukin-2 (40 U/ml) in RPMI 1640, 20% foetal calf serum. For infection with the infectious HIV, PBLs were pelleted and the cell pellet was then suspended in 1 ml of HIV virus adsorption solution and incubated at 37° C for 1 hour.

Alternatively, HIV-susceptible H9 cells were employed instead of normal human blood lymphocytes for testing of the antiviral effects of the compounds according to the invention.

The virus adsorption solution was centrifuged and the infected cell pellet was taken up in growth medium such that a concentration of 1×10$^5$ cells per ml was set. The cells infected in this way were pipetted at 1×10$^4$ cells/well into the wells of 96-well microtitre plates.

The first vertical row of the microtitre plate contained only growth medium and cells which had not been infected but otherwise treated exactly as described above (cell control). The second vertical row of the microtitre plate contained only HIV-infected cells (virus control) in growth medium. The other wells contained the compounds according to the invention at different concentrations, starting from the wells of the 3rd vertical row of the microtitre plate, from which the test substances were diluted 2$^{10}$ times in steps of 2.

The test batches were incubated at 37° C until the syncytia formation typical of HIV occurred in the untreated virus control (between day 3 and 6 after infection), which was then assessed microscopically. In the untreated virus control, about 20–50 syncytia resulted under these test conditions, while the untreated cell control contained no syncytia.

The IC$_{50}$ values were determined as the concentration of the treated and infected cells at which 50% (about 10–20 syncytia) of the virus-induced syncytia were suppressed by the treatment with the compound according to the invention.

It has now been found that the compounds according to the invention protect HIV-infected cells from virus-induced cell destruction.

TABLE 2

| Ex. No. | IC$_{50}$ (µM, PBL cell culture) |
|---|---|
| 30 | 10 |
| 31 | 10 |

The compounds of the general formulae (I) and (Ia) according to the invention are useful active compounds in human and veterinary medicine for the treatment and prophylaxis of disorders caused by retroviruses.

Examples of indication areas in human medicine which can be mentioned are:

1) The treatment and prophylaxis of human retrovirus infections.
2) For the treatment or prophylaxis of disorders (AIDS) caused by HIV I (human immunodeficiency virus; formerly called HTLV III/LAV) and HIV II and the stages associated therewith such as ARC (AIDS-related complexes) and LAS (lymphadenopathy syndrome) as well as the immunodeficiency and encephalopathy caused by this virus.
3) For the treatment or the prophylaxis of an HTLV-I or HTLV-II infection.
4) For the treatment or the prophylaxis of the AIDS-carrier state (AIDS-transmitter state).

Examples of indications in veterinary medicine which can be mentioned are:

Infections with
a) Maedi-visna (in sheep and goats)
b) progressive pneumonia virus (PPV) (in sheep and goats)
c) caprine arthritis encephalitis virus (in sheep and goats)
d) Zwoegersiekte virus (in sheep)
e) infectious anaemia virus (of the horse)
f) infections caused by feline leukaemia virus
g) infections caused by feline immunodeficiency virus (FIV)
h) infections caused by simian immunodeficiency virus (SIV)

The abovementioned items 2, 3 and 4 are preferred from the indication area in human medicine.

The present invention includes pharmaceutical preparations which, in addition to non-toxic, inert pharmaceutically suitable excipients, contain one or more compounds of the formulae (I) and (Ia) or which consist of one or more active compounds of the formulae (I) and (Ia), and processes for the production of these preparations.

The active compounds of the formulae (I) and (Ia) should be present in the abovementioned pharmaceutical preparations in a concentration of about 0.1 to 99.5% by weight, preferably of about 0.5 to 95% by weight, of the total mixture.

In addition to the compounds of the formulae (I) and (Ia), the abovementioned pharmaceutical preparations can also contain other pharmaceutical active compounds.

The abovementioned pharmaceutical preparations are produced in a customary manner according to known methods, e.g. by mixing the active compound or compounds with the excipient or excipients.

In general, it has proven advantageous both in human and in veterinary medicine to administer the active compound or compounds according to the invention in total amounts from about 0.5 to about 500 mg/kg, preferably 1 to 100 mg/kg, of body weight every 24 hours, if appropriate in the form of a plurality of individual doses, to achieve the desired results. An individual dose contains the active compound or compounds preferably in amounts from about 1 to about 80 mg/kg, in particular 1 to 30 mg/kg, of body weight. However, it may be necessary to depart from the doses mentioned, namely depending on the species and the body weight of the subject to be treated, the nature and severity of the disorder, the type of preparation and the administration of the medicament and the period or interval within which administration takes place.

Starting Compounds

EXAMPLE I

N-(1-Benzyl-4-piperidyl)-N'-phenylurea

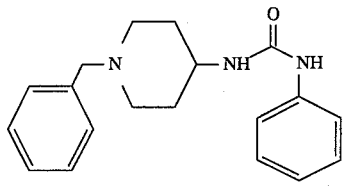

1.14 ml (10.5 mmol) of phenyl isocyanate are slowly added dropwise to a solution of 1.90 g (10.0 mmol) of 4-amino-1-benzylpiperidine and 1.46 ml (10.5 mmol) of triethylamine in 40 ml of dichloromethane. The reaction mixture may subsequently be stirred at room temperature for 1 h, and is then evaporated to dryness in vacuo. The residue is mixed with 50 ml of diethyl ether, stirred well, separated off by filtration, washed with 5 ml of diethyl ether and dried in a high vacuum. 2.62 g (85%) of the title compound are obtained as colourless crystals.

M.p.: 161°–162.5° C. $R_f$=0.24 (dichloromethane/methanol (9:1)) MS (FAB)m/e: 310 (M+H)$^+$

EXAMPLE II

N-(4-Piperidyl)-N'-phenylurea

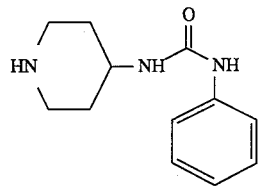

A suspension of 2.48 g (8.00 mmol) of the compound from Example I in a mixture of 38 ml of ethanol and 3.8 ml of water is treated with 1.26 g (20.0 mmol) of ammonium formate and then with 1.26 g of palladium on carbon and heated at 50° C. for 1 h. The reaction mixture may then be cooled. The solid portion is separated off by filtration and washed with 5 ml of ethanol. The filtrate is concentrated to dryness in vacuo, and the residue is triturated with diethyl ether, filtered off with suction, washed with 5 ml of diethyl ether and dried in a high vacuum. 1.53 g (87%) of the title compound are obtained as colourless crystals.

M.p.: 160–161° C. $R_f$=0.01 (dichloromethane/methanol (8:2)) MS (FAB) m/e: 220 (M+H)$^+$ As described for Example I, reaction of 4-amino-1-benzylpiperidine with various isocyanates gives the products shown in Table I:

TABLE I

| Ex. No. | R$^5$ | Yield (%) | MS (FAB) m/e (M + H)$^+$ | $R_f$/mobile phase ratio[b] | M.p. (°C.) |
|---|---|---|---|---|---|
| III | 4-CH$_3$—C$_6$H$_4$— | 98 | 323[a] | 0.27,I (9:1) | 199 |
| IV | 3-CF$_3$—C$_6$H$_4$— | 87 | 377[a] | 0.30,I (9:1) | 179 |
| V | 4-CF$_3$C$_6$H$_4$— | 64 | 377[a] | 0.25,I (9:1) | 158 |
| VI | 2-F,4-F—C$_6$H$_4$— | 70 | 345[a] | 0.26,I (9:1) | 159 |
| VII | 4-H$_5$C$_2$OOC—C$_6$H$_4$— | 91 | 382 | 0.32,I (9:1) | 125 |
| VIII | naphthyl | 97 | 360 | 0.31,I (9:1) | 194 |
| IX | 4-CH$_3$CO—C$_6$H$_4$ | 95 | 352 | 0.19,I (9:1) | 138 |
| X | 3-CH$_3$OOC—,5-CH$_3$OOC—C$_6$H$_4$— | 92 | 426 | 0.26,I (9:1) | 106 |
| XI | 4-H$_5$C$_2$OOC—CH=CH—C$_6$H$_4$— | 95 | 408 | 0.60,I (9:1) | 177 |

[a] MS (EI, 70 ev) m/e (M)$^+$
[b] I = Dichloromethane/methanol

As described for Example II, the corresponding starting materials give the products shown in Table II:

TABLE II

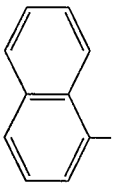

| Ex. No. | R⁵ | Yield (%) | MS (FAB) m/e (M + H)⁺ | M.p. (°C.) | Starting material from Example |
|---|---|---|---|---|---|
| XII | 4-CH$_3$—C$_6$H$_4$— | 70 | 234 | 178 | III |
| XIII | 3-CF$_3$—C$_6$H$_4$— | 80 | 288 | 139 | IV |
| XIV | 4-CF$_3$—C$_6$H$_4$— | 83 | 288 | 187 | V |
| XV | 2-F—,4-F—C$_6$H$_4$— | 76 | 256 | 172 | VI |
| XVI | 4-H$_5$C$_2$OOC—C$_6$H$_4$— | 86 | 292 | 173 | VII |
| XVII | naphthyl | 65 | 270 | 191 | VIII |
| XVIII | 4-CH$_3$CO—C$_6$H$_4$ | 68 | 262 | amorphous powder | IX |
| XIX | 3-CH$_3$OOC—,5-CH$_3$OOC—C$_6$H$_4$— | 61 | 336 | 240 | X |
| XX | 4-H$_5$C$_2$OOC—CH=CH—C$_6$H$_4$—ᵃ⁾ | 66 | 320 | 123 | XI |

ᵃ⁾During the removal of the benzyl group saturation of the double bond takes place simultaneously Preparation Examples

Example 1

8-Methoxy-2-[4-(phenylaminocarbonyl-amino)piperidylcarbonyl]-chroman

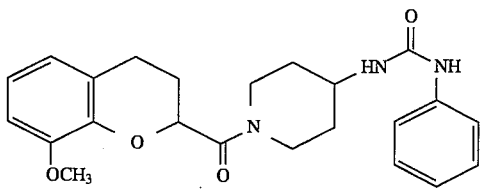

A solution, cooled to 0° C., of 770 mg (3.51 mmol) of 8-methoxychromancarboxylic acid and 586 mg (3.83 mmol) of 1-hydroxybenzotriazole in 20 ml of anhydrous dichloromethane is treated with 723 mg (3.51 mmol) of dicyclohexylcarbodiimide and stirred for 5 min. A solution of 700 mg (3.19 mmol) of the compound from Example II and 0.88 ml (8.00 mmol) of N-methylmorpholine in 20 ml of dichloromethane is then added dropwise, and the reaction mixture may be stirred at room temperature for 1 h. The resultant urea is then removed by filtration, the filtrate is concentrated in vacuo and the crude product is purified by chromatography on 150 g of silica gel (dichloromethane/methanol 95:5). The product-containing fractions are collected, the solvent is evaporated in vacuo, and the residue is triturated with diethyl ether, filtered off with suction and dried in a high vacuum. 1.24 g (95%) of the title compound are obtained as colourless crystals.

M.p.: 215°–216° C. R$_f$=0.17 (dichloromethane/methanol (95:5)) MS (FAB) m/e: 410 (M+H)⁺

Example 2

8-Methoxy-2-[4-(phenylaminocarbonyl-amino)piperidylmethyl]-chroman

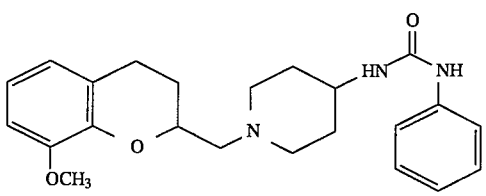

10.0 ml (10.00 mmol) of a 1M solution of borane in THF are added dropwise to a stirred solution of 819 mg (2.00 mmol) of the compound from Example 1 in 25 ml of anhydrous tetrahydrofuran. The reaction mixture is stirred at room temperature for 1 h, introduced into 40 ml of 5N HCl and heated at 90° C. for 15 min. After cooling, it is adjusted to pH 11 with concentrated sodium hydroxide solution and extracted twice with 20 ml of ethyl acetate. The combined organic extracts are dried over MgSO$_4$, concentrated in vacuo and purified by chromatography on 25 g of silica gel (dichloromethane/methanol 9:1). 659 mg (83%) of the title compound are obtained as colourless crystals.

M.p.: 163° C. R$_f$=0.29 (dichloromethane/methanol (9:1)) MS (FAB) m/e:=396 (M+H)⁺

As described for Example 1, condensation of 8-methoxy-chromancarboxylic acid with the corresponding starting materials gives the products shown in Table 1:

TABLE 1

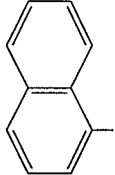

| Ex. No. | R⁵ | Yield (%) | MS (FAB) m/e (M + H)⁺ | $R_f$/mobile phase* ratio | M.p. (°C.) | Starting material from Example |
|---|---|---|---|---|---|---|
| 3 | 4-$CH_3$—$C_6H_4$— | 41 | 424 | 0.49,I (95:5) | 196 | XII |
| 4 | 3-$CF_3$—$C_6H_4$— | 73 | 478 | 0.52,I (9:1) | 203 | XIII |
| 5 | 4-$CF_3$—$C_6H_4$— | 76 | 478 | 0.43,I (9:1) | 113 | XIV |
| 6 | 2-F—,4-F—$C_6H_4$— | 95 | 446 | 0.57,I (9:1) | 200 | XV |
| 7 | 4-$H_5C_2OOC$—$C_6H_4$— | 29 | 482 | 0.33,I (9:1) | 143 | XVI |
| 8 | naphthyl | 31 | 460 | 0.43,I (9:1) | 218 | XVII |
| 9 | 4-$CH_3CO$—$C_6H_4$ | 64 | 452 | 0.44,I (9:1) | 178 | XVIII |
| 10 | 3-$CH_3OOC$—,5-$CH_3OOC$—$C_6854YH_4$— | 76 | 526 | 0.41,I (9:1) | 186 | XIX |
| 11 | 4-$H_5C_2OOC$—CH=CH—$C_6H_4$— | 37 | 510 | 0.53,I (9:1) | 135 | XX |

*I = Dichloromethane/methanol

As described for Example 2, reduction of the corresponding amides (starting materials) gives the products shown in Table 2:

TABLE 2

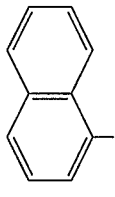

| Ex. No. | R⁵ | Yield (%) | MS (FAB) m/e (M + H)⁺ | $R_f$/mobile phase^b) ratio | M.p. (°C.) | Starting material from Example |
|---|---|---|---|---|---|---|
| 12 | 4-$CH_3$—$C_6H_4$— | 59 | 410 | 0.35,I (9:1) | 169 | 3 |
| 13 | 3-$CF_3$—$C_6H_4$— | 68 | 464 | 0.40,I (9:1) | 168 | 4 |
| 14 | 4-$CF_3C_6H_4$— | 77 | 464 | 0.37,I (9:1) | 169 | 5 |
| 15 | 2-F—,4-F—$C_6H_4$— | 57 | 431 | 0.35,I (9:1) | 183 | 6 |
| 16 | 4-$H_5C_2OOC$—$C_6H_4$— | 59 | 468 | 0.39,I (9:1) | 178 | 7 |
| 17 | naphthyl | 67 | 446 | 0.24,I (9:1) | 185 | 8 |
| 18 | 4-$CH_3$—$CH_2$—$C_6H_4$—^a) | 40 | 424 | 0.13,I (9:1) | 171 | 9 |
| 19 | 3-$CH_3OOC$,5-$CH_3OOC$—$C_6H_4$— | 41 | 512 | 0.41,I (9:1) | 179 | 10 |
| 20 | 4-HO—$(CH_2)_3$—$C_6H_4$—^a) | 24 | 454 | 0.24,I (9:1) | oil | 11 |

^a)Additionally reduced to the amide
^b)Dichloromethane/methanol

As described for Example 1, condensation of the corresponding chromancarboxylic acids with 4-(2-oxo-1-benzimidazolinyl) piperidine gives the products shown in Table 3:

TABLE 3

[Structure shown: chroman with piperidinyl-benzimidazolone substituent; positions labeled A and *]

| Ex. No. | A | * | MS (FAB) m/e (M + H)+ | R_f/mobile phase a) | Yield |
|---|---|---|---|---|---|
| 21 | H | Racemate | 378 | 0.47,II | 87% |
| 22 | H | (S)-Enantiomer | 378 | 0.47,II | 83% |
| 23 | H | (R)-Enantiomer | 378 | 0.47,II | 79% |
| 24 | OCH₃ | Racemate | 408 | 0.42,II | 85% |
| 25 | OCH₃ | (S)-Enantiomer | 408 | 0.42,II | 84% |
| 26 | OCH₃ | (R)-Enantiomer | 409 | 0.42,II | 90% | a) II - Ethyl acetate/acetone 5:3

As described for Example 2, reduction of the amides gives the products shown in Table 4:

TABLE 4

[Structure shown: chroman with methylene-piperidinyl-benzimidazolone substituent; positions labeled A and *]

| Ex. No. | A | * | MS (FAB) m/e (M + H)+ | R_f/mobile phase a) | [α]_D | Yield | Starting material from example |
|---|---|---|---|---|---|---|---|
| 27 | H | Racemate | 364 | 0.26,II | — | 77% | 21 |
| 28 | H | (S)-Enantiomer EE > 99% | 364 | 0.26,II | +53.9 (c = 0.6 THF) | 74% | 22 |
| 29 | H | (R)-Enantiomer EE > 99% | 364 | 0.26,II | −51.2 (c = 0.6, THF) | 83% | 23 |
| 30 | OCH₃ | Racemate | 394 | 0.21,II | — | 75% | 24 |
| 31 | OCH₃ | (S)-Enantiomer EE > 99% | 394 | 0.21,II | +47.0° (c = 1, CHCl₃) | 89% | 25 |
| 32 | OCH₃ | (R)-Enantiomer EE > 99% | 394 | 0.21,II | −50.5° (c = 1, CHCl₃) | 85% | 26 | a) II = Ethyl acetate/acetone 5:3

EXAMPLE 33

8-Hydroxy-2-[4-(2-oxo-1-benzimidazolyl)piperidylmethyl]-chroman

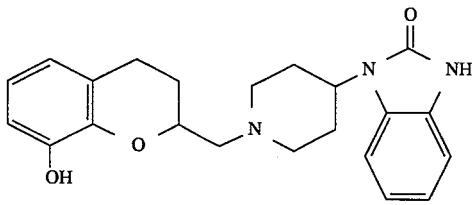

1 g (2.54 mmol) of the methyl ether from Example 30 is heated under reflux for 3 h in 20 ml of hydrobromic acid. The mixture is then rendered alkaline using half-concentrated sodium hydroxide solution and extracted 3 times with ethyl acetate, and the combined organic phases are dried (MgSO₄) and concentrated. The residue is chromatographed on silica gel using dichloromethane/methanol (40:1) as the eluent.

Yield:97% R_f=0.31 (dichloromethane/methanol 10:1) MS (EI): m/e=379 (M+H)+

Example 34

8-Ethoxy-2-[4-(2-oxo-1-benzimidazolyl)piperidylmethyl]-chroman

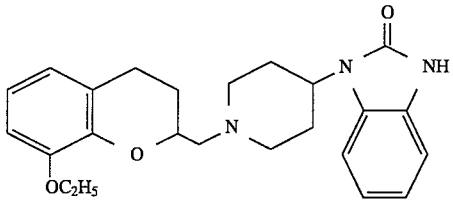

50 mg(0.13 mmol) of the compound form Example 33 are dissolved in 1 ml of dimethylformamide. 4 mg(0.13 mmol) of sodium hydride and 11 μl(0.13 mmol) of ethyl iodide are added at 0° C., and the mixture is stirred at 0° C. for 3 h, diluted with water and extracted 3 times with ether. The organic phase is dried (MgSO₄) and concentrated. The residue is then chromatographed on silica gel using dichloromethane/methanol (50:1) as the eluent.

Yield: 14% R_f=0.18 (dichloromethane/methanol 20:1) MS (EI): m/e=407(M+H)³⁰

We claim:
1. A compound of the formula

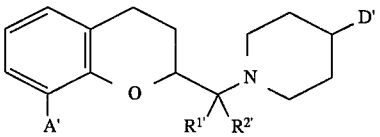

(Ia)

in which
A' represents hydrogen, hydroxyl or straight-chain or branched alkoxy having up to 8 carbon atoms,
R¹' and R²' represents hydrogen, and D represents —NR$^{3'}$—CO—NR$^{4'}$R$^{5'}$ or
R$^{1'}$ and R$^{2'}$ together represent the —C=O group,
D represents a radical of the formula

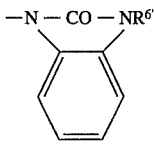

in which
R$^{3'}$, R$^{4'}$ and R$^{6'}$ are identical or different and denote hydrogen or straight-chain or branched alkyl having up to 6 carbon atoms,
R$^{5'}$ denotes aryl having 6 to 10 carbon atoms, which is optionally substituted up to 3 times by identical or different substituents from the series consisting of halogen, hydroxyl, carboxyl, trifluoromethyl and trifluoromethoxy, by straight-chain or branched acyl, alkoxy or alkoxycarbonyl in each case having up to 8 carbon atoms or by straight-chain or branched alkyl or alkenyl in each case having up to 8 carbon atoms, which for their part can be substituted by hydroxyl or carboxyl or by straight-chain or branched alkoxy or alkoxycarbonyl in each case having up to 6 carbon atoms, its racemate, enantiomer and salt.

2. A pharmaceutical composition comprising a therapeutically effective amount of a compound according to claim 1 and a pharmaceutically acceptable diluent.

* * * * *